United States Patent [19]

Adams et al.

[11] Patent Number: 4,534,958

[45] Date of Patent: Aug. 13, 1985

[54] AEROSOL GEL

[75] Inventors: Dennis V. Adams, Grosse Pointe Farms; Norbert J. Cremers, Grosse Pointe; Raymond L. Henry, Grosse Pointe Woods, all of Mich.

[73] Assignee: BASF Wyandotte Corporation, Wyandotte, Mich.

[21] Appl. No.: 513,439

[22] Filed: Jul. 13, 1983

[51] Int. Cl.³ .............................................. A61K 9/00
[52] U.S. Cl. ........................................ 424/45; 424/78; 514/944
[58] Field of Search .................................... 424/45, 78

[56] References Cited

U.S. PATENT DOCUMENTS

| | | | |
|---|---|---|---|
| 2,674,619 | 4/1954 | Lundsted | 260/485 |
| 2,677,700 | 5/1954 | Jackson et al. | 260/488 |
| 3,476,853 | 11/1969 | Jatul et al. | 424/45 |
| 3,639,575 | 2/1972 | Schmolka | 424/78 |
| 3,751,562 | 8/1973 | Nichols | 424/45 |
| 4,293,542 | 10/1981 | Lang et al. | 426/47 |

FOREIGN PATENT DOCUMENTS 1444334   7/1976   United Kingdom .

OTHER PUBLICATIONS

Chemical Abstracts, 82: 45617r, (1975), (Veltman).
Handbook of Nonprescription Drugs, 5th Ed., 1977, pp. 277-279.

*Primary Examiner*—Leonard Schenkman
*Attorney, Agent, or Firm*—Bernhard R. Swick

[57] ABSTRACT

A pressurized composition in an aerosol container and adapted to form a spray upon release of pressure therefrom which composition is a liquid inside the container and forms a gel on contact with living tissue comprising water, propellant, volatile solvent and a polyoxyethylene-polyoxypropylene copolymer. The preferred composition may also advantageously include a skin treating agent, and conventional skin treatment additives.

6 Claims, No Drawings

AEROSOL GEL

BACKGROUND OF THE INVENTION

1. Field of the Invention

The present invention relates to a sprayable aerosol foam treatment composition which is a liquid in the aerosol container and forms a gel upon application to the skin.

2. Prior Art

The treatment of burns with medicated liquid such as silver ion solutions is well known in the art as evidenced by Moyer et al, *Arch, Surg.* 90, June, 1965. Briefly, the known treatments of burns comprise applying a solution of medication such as a silver nitrate solution to a burn wound. Because this treatment involves liquid solutions, it is known as a wet dressing method. The conventional wet dressing method suffers from many disadvantages. Some of these include (1) exacerbation of the hypermetabolic state by increasing caloric deficit and heat loss, (2) loss of plasma water, serum protein, and serum electrolytes, (3) maseration of burn wound surfaces, (4) increase of fluid loss by vaporization, (5) extensive nursing care, (6) economic loss due to discoloration of bedding, equipment, floors and walls. With so many disadvantages, it is not surprising that the art has searched for an alternate method of treating burns.

U.S. Pat. No. 3,639,575 discloses compositions prepared from aqueous gels of polyoxyethylene-polyoxypropylene block copolymers as a matrix for silver ions for burn treatment.

U.S. Pat. No. 3,751,562, discloses an aerosol gel formulation employing an oxyethylated fatty alcohol, mineral oil, iodine and water.

U.S. Pat. No. 4,293,542, discloses aerosol formulations which can be an aqueous gel containing oxyethylated fatty alcohols and a gel-forming agent and, as an essential component, a pyridine derivative.

British Pat. No. 1,096,357 discloses an aerosol gel comprising a partial fatty acid soap of a polyvalent metal hydroxide, a nonpolar oil along with propellants.

British Pat. No. 1,444,334 discloses an aerosol gel composition which may be employed as a shaving cream composition and which contains as a gelling agent a polyoxypropylene-polyoxyethylene block copolymer. An essential component of the composition is a water-soluble soap.

In U. S. Pat. No. 3,476,853, a sprayable composition for use as a dressing including a film-forming material, an opacifying material, at least one medicament, a solvent and a gaseous propellant is disclosed. The fluid dressing or bandage is applied by spraying the fluid dressing from a closed pressure-resistant container by the expansion of a normally gaseous propellant in liquid state. The patent discloses a means for applying a protective opaque film which is immediately dry to the touch when applied from a distance of 4 to 6 inches. This provides a simulated bandage.

SUMMARY OF THE INVENTION

In accordance with the instant invention, improved foam treatment is achieved by the use of a pressurized composition which may be sprayed from an aerosol container and which is liquid inside the container and forms a gel on contact with living tissue such as the skin of a burn victim. This is accomplished by the combination of water, propellant, volatile solvent and certain polyoxyethylene-polyoxypropylene block copolymers. The composition may also contain at least one burn treatment agent in an effective amount. The copolymers have a molecular weight for the polyoxypropylene hydrophobe of 2250 to 4000 and an oxyethylene content of 50 to 90 percent by weight of the copolymer.

DESCRIPTION OF THE PREFERRED EMBODIMENTS

The aerosol composition of the instant invention comprises by weight about 35 to 80 percent water, about 3 to 50 percent and preferably about 5 to 15 percent propellant, about 10 to 25 percent, preferably about 15 to 20 percent of the polyoxyethylene-polyoxypropylene copolymer, about 1 to 10 percent of the volatile solvent, 0 to about 10 percent, preferably about 0.05 to 5 percent, of a burn treatment agent, and 0 to 10 percent, preferably about 1.0 to 5.0 percent of other additives.

The polyoxyethylene-polyoxypropylene block copolymer of use in the invention is a cogeneric mixture of conjugated polyoxyethylene-polyoxypropylene compounds corresponding to the following formula:

$$HO(C_2H_4O)_m(C_3H_6O)_n(C_2H_4O)_mH$$

wherein n has a value such that the molecular weight of the polyoxypropylene hydrophobe base is about 2250 to 4000 and m represents from about 50 to 90 weight percent of the molecule. The oxypropylene chains optionally, but advantageously, contain small amounts of oxyethylene and oxybutylene groups and the oxyethylene chains also optionally, but advantageously, contain small amounts of oxypropylene and oxybutylene groups. These compositions are more particularly described in U.S. Pat. Nos. 2,677,700, and 2,674,619.

A composition which is a liquid inside the container and forms a gel on contact with living tissue is achieved by including a volatile solvent in the composition. Such solvents include alcohols such as methyl, ethyl and propyl, ketones such as acetone, ethers such as methyl, ethyl, methyl-ethyl, dimethyl, diethyl and similar ethers, liquid polyethylene glycols, propylene glycol, dipropylene glycol and dichloromethane.

The propellant can be any one or a blend of the following as examples: propane, isobutane and other petroleum distillates, nitrogen, carbon dioxide, dimethylether, ethylmethylether, methylene chloride, vinyl chloride and fluorochlorohydrocarbons. The latter include Freon 115 pentafluorochloroethane and Freon C-318, octafluorocyclobutane.

A burn treatment composition may include one or more medicaments. The burn treatment medication may be any water-soluble or water-insoluble salt as well as other drugs conventionally used for treatment of burns. Suitable salts would include the nitrates, lactates, acetates, sulfadiazine and other salts of silver or other heavy metals. Antibiotics may also be used such as bacitracin, neomycin, erythromycin, streptomycin, paramycin, bacteriostats such as garamycin, wound healing agents such as piracetam, aloe vera, and other compositions and compounds normally used to speed up burn healing. In general, the composition would contain from about 0.05 to 5 percent by weight of the burn treatment medication.

While a medicament is desirable and is often employed in a burn treatment gel as described, the principal feature of the burn treatment gel is the protection of the burn or wound which can be accomplished without the inclusion of a medicating agent.

Many and various other ingredients are generally also included in these gels. Other components could include proteins, amino acids, electrolytes and other ingredients normally found in body fluids. Humectants, such as propylene glycol or glycerine, may also be included. Further adjuvents could include silicone oils. Also, other ingredients which impart further desired qualities to the skin may be incorporated in the compositions of the invention, e.g., skin fresheners or lather stabilizers or the like such as lanolin or its derivatives, lecithin, higher alcohols, dipelargonate ethers or esters, coconut oil and other fatty esters and mixtures thereof may generally be used in minor proportions. Furthermore, coloring materials such as dyes and perfumes may be used, if desired. The amount of other additives would range from 0 to about 10 percent by weight and preferably from about 1.0 to 5 percent by weight.

The following examples are included to further illustrate the present invention. Unless otherwise stated, throughout the application, all parts and percentages are by weight and all temperatures are in degrees centigrade.

EXAMPLE 1

A gel concentrate was prepared from 20 parts of a polyoxyethylene-polyoxypropylene block copolymer of the type shown in the above formula having a molecular weight of the polyoxypropylene hydrophobe of 4000 and containing 70 percent by weight oxyethylene groups, 3 parts propylene glycol and 77 parts water. Fifty-two parts of this gel concentrate and 6 parts of isopropanol were placed in an aerosol container having a Newman Green B-14-B valve and a 120-20-18 activator. This resulted in the formation of a homogeneous liquid. Thirty-five parts by weight of dimethylether propellant were then added through the valve. The contents were shaken and sprayed onto a patch of human skin.

The spray temperature as it leaves the valve was measured with a thermocouple and found to be 34.7° F. initially and 40.5° F. when 80 percent empty. A thin film formed initially after which the dimethylether and isopropanol evaporated forming a coating on the skin. This became a foamy gel as the solvent and propellant evaporated providing protection for the burn.

EXAMPLE 2

Example 1 was repeated with the exception that the aerosol container had a Precision valve with a 0.024 stem, a 0.025 body, and a 0.013 vapor tap and the actuator was a 0.016 MBRT actuator. The spray temperature as it leaves the valve was measured with a thermocouple and found to be 40.1° F. initially and 34.3° F. when 80 percent empty. A thin film formed initially after which the dimethylether and isopropanol evaporated forming a coating on the skin. This became a foamy gel as the solvent and propellant evaporated providing protection for the burn.

EXAMPLE 3

One hundred parts of a solution comprising 16.4 parts of the copolymer of Example 1, 5.0 parts isopropanol, 0.1 part chlorhexidine, 2.0 parts glycerine, and 76.5 parts water are placed in an aerosol container similar to that described in Example 1. The container is pressurized and sealed with a valve and 50 parts of carbon dioxide propellant added to the aerosol container through the valve. When sprayed from the aerosol container onto the forearm of a human, a coating forms on the skin. This becomes a foamy gel as the solvent and propellant evaporate, providing protections for the burn.

EXAMPLE 4

Example 3 is repeated substituting a polyoxyethylene-polyoxypropylene copolymer of the type shown in the formula above having a molecular weight of the hydrophobe of about 3250 and containing about 80 percent by weight oxyethylene groups for the copolymer of Example 1. When sprayed from the aerosol container onto the forearm of a human, a coating forms. This becomes a foamy gel as the solvent and propellant evaporate providing protection for the burn.

EXAMPLE 5

Example 3 is repeated with the exception that 1.0 parts by weight of silver nitrate was employed in lieu of the chlorhexidine, 0.5 part neomycin was included and the amount of the copolymer was reduced to 15.0 parts. When sprayed from the aerosol container onto the forearm of a human, a coating forms. This becomes a foamy gel as the solvent and propellant evaporate providing protection for the burn.

The embodiments in which an exclusive privilege or property is claimed are defined as follows:

1. A pressurized composition in an aerosol container capable of forming a spray upon release of pressure therefrom which composition is a liquid inside the container and forms a gel on contact with living tissue comprising by weight about 35 to 80 percent water, 3 to 50 percent propellant, 1 to 10 percent volatile solvent and 10 to 25 percent of a polyoxyethylene-polyoxypropylene copolymer of the formula:

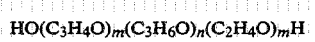
$$HO(C_3H_4O)_m(C_3H_6O)_n(C_2H_4O)_mH$$

wherein n is an integer; the value of which is such that the molecular weight of the oxypropylene groups is from about 2250 to 4000; and the value of m is such that the oxyethylene groups constitute about 50 to 90 percent by weight of the compound.

2. The composition of claim 1 wherein said composition includes about 0.05 to 5 percent by weight burn treatment medication.

3. The composition of claim 2 including about 1.0 to 10 percent of at least one additional adjuvant.

4. A process for treating living skin comprising spraying a gel composition in liquid form onto living skin, whereby a gel is formed on contact therewith, said composition comprising by weight about 35 to 80 percent water, about 3 to 50 percent propellant, about 1 to 10 percent volatile solvent, and about 10 to 25 percent of a polyoxyethylene-polyoxypropylene copolymer of the formula

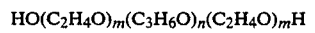
$$HO(C_2H_4O)_m(C_3H_6O)_n(C_2H_4O)_mH$$

wherein n is an integer; the value of which is such that the molecular weight of the oxypropylene groups is from about 2250 to 4000; and the value of m is such that the oxyethylene groups constitute about 50 to 90 percent by weight of the compound.

5. The process of claim 4 wherein said composition about 0.05 to 10 percent burn treatment medication.

6. The process of claim 5 wherein said composition includes about 1.0 to 10 percent by weight of at least one additional adjuvant.

* * * * *

UNITED STATES PATENT AND TRADEMARK OFFICE
CERTIFICATE OF CORRECTION

PATENT NO. : 4,534,958
DATED : August 13, 1985
INVENTOR(S) : Dennis V. Adams, Norbert J. Cremers & Raymond L. Henry It is certified that error appears in the above-identified patent and that said Letters Patent is hereby corrected as shown below:

Claim 1, revise formula to read as follows:

$$HO(C_2H_4O)_m(C_3H_6O)_n(C_2H_4O)_mH$$

Signed and Sealed this

Tenth Day of December 1985

[SEAL]

Attest:

DONALD J. QUIGG

Attesting Officer

Commissioner of Patents and Trademarks